United States Patent
Cho et al.

(10) Patent No.: US 8,476,046 B2
(45) Date of Patent: Jul. 2, 2013

(54) METHOD OF PRE-TREATING AND SACCHARIFYING ALGAE BIOMASS

(75) Inventors: Hwa Young Cho, Hwaseong-si (KR); Jun Seok Kim, Suwon-si (KR); Jae Chan Park, Yongin-si (KR); Sung Min Park, Yongin-si (KR); Jin Woo Kim, Bucheon-si (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 523 days.

(21) Appl. No.: 12/488,682

(22) Filed: Jun. 22, 2009

(65) Prior Publication Data

US 2010/0209976 A1    Aug. 19, 2010

(30) Foreign Application Priority Data

Feb. 16, 2009 (KR) .................. 10-2009-0012359

(51) Int. Cl.
*C12P 19/02* (2006.01)
(52) U.S. Cl.
USPC ........... 435/105; 435/134; 435/150; 435/157; 435/160; 435/161
(58) Field of Classification Search
None
See application file for complete search history.

(56) References Cited

FOREIGN PATENT DOCUMENTS

| JP | 2001-205070 | 7/2001 |
|---|---|---|
| JP | 2003-310288 | 11/2003 |
| JP | 2008-011721 | 1/2008 |
| KR | 1020080091257 | 10/2008 |

OTHER PUBLICATIONS

Nguyen et al., J. Microbiol.Biotechnol., 2008, vol. 19, No. 2, p. 161-166.*
Kim et al., Bioresource Technology, 2002, vol. 83, p. 165-171.*
Roos, C.J., 2008, Biomass Drying and Dewatering for Clean & Power, 30 pages of PDf.*
Molina Grima et al., Biotechnology Advances, 2003, Vo. 20, p. 491-515.*
Toda et al., Nature, 2005, vol. 438, p. 178.*

* cited by examiner

*Primary Examiner* — Kade Ariani
(74) *Attorney, Agent, or Firm* — Leydig, Voit & Mayer, Ltd.

(57) ABSTRACT

Disclosed is a method of pre-treating and saccharifying an algae biomass, by dehydrating the algae biomass to have a water content of about 10% to about 70% by weight, cutting the algae biomass having a water content of about 10% to about 70% by weight to a predetermined size, and saccharifying the cut algae biomass using a hydrolysis catalyst and/or a hydrolase to yield a monosaccharide.

14 Claims, 2 Drawing Sheets

METHOD OF PRE-TREATING AND SACCHARIFYING ALGAE BIOMASS

CROSS-REFERENCE TO RELATED APPLICATION

This application claims priority to Korean Patent Application No. 2009-12359, filed on Feb. 16, 2009, and all the benefits accruing therefrom under 35 U.S.C. §119, the contents of which in its entirety are herein incorporated by reference.

BACKGROUND

1. Field

Exemplary embodiments relate to a method of pre-treating and saccharifying an algae biomass, a method of producing biofuel using monosaccharide obtained by the method, and technology associated with algae biomass pre-treating and a saccharifying apparatus.

2. Description of the Related Art

With globally increasing concern about exhaustion of resources and pollution of the environment due to overuse of fossil fuels, the development of novel and renewable alternative energy sources that stably and continuously produce energy is of paramount importance. As a part of the development of such alternative energies, technology for producing energy from biomass has been attracting considerable attention.

Today, first generation biofuels using saccharides such as sugar cane or starches such as corn are being produced. However, these strategies face the problems of competition from food and livestock feed, and saturation of agricultural land. For these reasons, second generation biofuels using lignocellulose, which comes from wood and is considered to be the most abundant, rich and renewable resource in the world, are being developed. However, lignocellulose is a complex of lignin, which is a non-degradable aromatic polymer, and cellulose and hemicellulose, which are carbohydrates. Thus, lignocellulose needs to be pre-treated to remove the lignin from the carbohydrates, which is complicated and relatively costly.

More recently, the development of biofuels using algae has begun. Since algae have the advantages of rapid growth, ease of mass-culturing and high absorption (consumption) of carbon dioxide, it is considered to be an appropriate and novel energy source. Since algae is less dense than lignin, it is more easily saccharified than biomass used for first and second generation biofuels, and can also be produced on a large scale. In addition, because relatively abundant marine resources can be utilized, there is great potential.

SUMMARY

In one embodiment, a method of pre-treating and saccharifying algae biomass is provided, the method includes: dehydrating the algae biomass to have a water content of about 10% to about 70% by weight; cutting the algae biomass having a water content of about 10% to about 70% by weight to a predetermined size; and saccharifying the cut algae biomass using a hydrolysis catalyst and/or a hydrolase to yield monosaccharide.

In another embodiment, a method of producing biofuel using monosaccharide yielded by the method of pre-treating and saccharifying algae biomass is provided. The biofuel may be prepared by fermenting the monosaccharide using a microorganism.

According to another embodiment, an apparatus for pre-treating and saccharifying algae biomass is provided, the apparatus including: a dehydrating apparatus including a hollow conduit through which algae biomass flows, an inlet disposed at one side of the conduit and inputting the algae biomass, a screw disposed in the hollow center of the conduit and providing a conveying force by axial rotation, and an outlet disposed at the other side of the conduit and outputting the algae biomass; a cutting apparatus including a cutter connected to an end of the outlet side of the dehydrating apparatus to cut the algae biomass; a saccharifying apparatus including a reaction vessel containing the algae biomass cut by the cutting apparatus to saccharify the algae biomass; and a vapor generating apparatus connected to the saccharifying apparatus to provide vapor to the saccharifying apparatus.

BRIEF DESCRIPTION OF THE DRAWINGS

Exemplary embodiments are described in further detail below with reference to the accompanying drawings. It should be understood that various aspects of the drawings may have been exaggerated for clarity.

DETAILED DESCRIPTION

Figure 1:
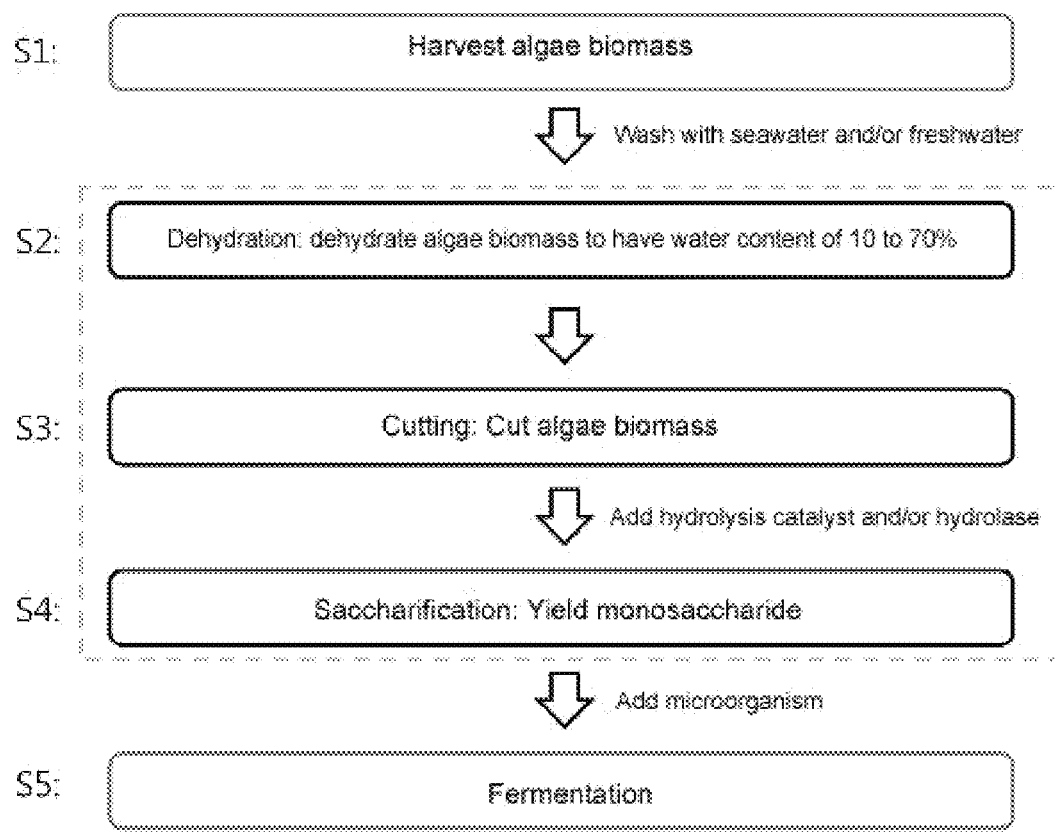
FIG. 1 is a flowchart showing an exemplary embodiment of a process including saccharification, pre-treatment and fermentation operations according to the disclosure.

Hereinafter, the inventive concept will be described more fully with reference to exemplary embodiments and the accompanying drawings. However, it should be understood that the inventive concept is not limited to the described exemplary embodiments, and may be embodied in various modifications and changes.

The exemplary embodiments of the invention may, however, maybe embodied in many different forms, and should not be construed as being limited to the embodiments set forth herein. Rather, these embodiments are provided so that this disclosure will be thorough and complete and will fully convey the concept of the invention to those skilled in the art, and the exemplary embodiments of the invention will only be defined by the appended claims. Like reference numerals refer to like elements throughout the specification.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. As used herein, the term "and/or" includes any and all combinations of one or more of the associated listed items.

As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention.

1. Method of Pre-treating and Saccharifying Algae Biomass

FIG. 1 is a flowchart showing a process of pre-treating and saccharifying algae biomass according to an exemplary embodiment. Referring to FIG. 1, the method of pre-treating and saccharifying algae biomass according to an exemplary embodiment may include: dehydrating the algae biomass to have a water content of about 10% to about 70% by weight (S2); cutting the algae biomass having a water content of about 10% to about 70% by weight to a predetermined size (S3); and saccharifying the cut algae biomass with a hydrolysis catalyst and/or a hydrolase to yield monosaccharide (S4).

The algae biomass is classified into red, brown and green algae, but the inventive concept is not limited thereto. The algae may be obtained directly from the ocean or by farming (S1).

The red algae may include, but is not limited to, *Gelidium amansii, Gracilaria verrucosa, Bangia atropurpurea, Porphyra suborbiculata, Porphyra yezoensis, Galaxaura falcate), Scinaia japonica, Gelidium divaricatum, Gelidium pacificum, Lithophylum okamurae, Lithothammion cystocarpideum, Amphiroa anceps, Amphiroa beauvoisii, Corallina officinalis, Corallina pilulifera, Marginisporum aberrans, Carpopeltis prolifera, Grateloupia filicina, Grateloupia elliptica, Grateloupia lanceolanta, Grateloupia turtuturu, Phacelocarpus japonicus, Gloiopeltis furcata, Hypnea charoides, Hypnea japonitca, Hypnea saidana, Chondrus cripspus, Chondracanthus tenellus, Gracilaria textorii, Lomentaria catenata, Heterosiphonia japonica, Chondria crassicaulis, Symphyocladia latiuscula, Porphyra yezoensis Ueda, Eucheuma Cottonii, Grateloupia lanceolata, Pterocladia tenuis, Acanthopeltis japonica, Gloiopeltis tenax, Irish moss, Pachymeniopsis elliptica, Ceramium kondoi, Ceramium boydenii, Gigartina tenella*, and *Campylaephora hypnaeoides*.

The green algae may include, but is not limited to, *Enteromorpha, Spirogyra* spp., *Codium fragile, Codium minus, Caulerpa okamurai*, and *Nostoc commune*.

The brown algae may include, but is not limited to, *Laminaria japonica, Undaria pinnatifida, Hizikia fusiforme, Analipus japonicus, Chordaria flagelliformis, Ishige okamurai, Scytosiphon lomentaria, Endarachne binghamiae, Ecklonia cava, Ecklonia stolonifera, Eisenia bicyclis, Costaria costata, Sargassum fulvellum, Sargassum horneri*, and *Sargassum thunbergii*.

Algae generally contain a large quantity of water, ranging from about 70 to 95% by weight. In conventional methods, a drying pre-treatment operation is performed to dry the algae to have a water content of nearly 0% by weight and then pulverizing the dried algae. That is, technology for producing biofuels by pre-treating, saccharifying and fermenting dried land plants was similarly applied to algae. However, such a drying and pulverizing operation results in an overuse of energy, an increase in production costs, and time and space restrictions due to the transport of an algae biomass from a farming and harvesting location to a drying and pulverizing treatment location.

On the other hand, according to an exemplary embodiment, a wet process for saccharifying an algae biomass which is not completely dried and still contains water may be utilized. Applicants have found that cutting the algae biomass to a predetermined size is an effective way to increase the specific surface area of the algae biomass which gives a higher saccharification rate, and the water content of the algae biomass can be reduced to be suitable for the cutting process. Thus, after the dehydration operation, the water content of the algae biomass may be about 10% to about 70% by weight or about 20% to about 60% by weight.

The dehydration operation may be performed at about 15 to 35° C. or room temperature for 0.5 to 100 minutes. Accordingly, since a high-temperature drying operation using a hot air dryer is not utilized, energy consumption and treatment time can be minimized.

The dehydration operation may be performed using a dehydrating apparatus having a screw providing conveying force by axial rotation. The dehydrating apparatus can remove water contained in the algae biomass due to centrifugal force resulting from the rotation of the screw. The water content of the algae biomass depends on rotation speed of the screw such that as the rotation speed of the screw is increased, the water content of the algae biomass is decreased. The algae biomass contacts an inner surface of the dehydrating apparatus during rotation, so that the surface of the algae biomass can be damaged due to friction force, which is a suitable physical treatment for saccharification.

The dehydrating apparatus may be, but is not limited to, one of apparatuses known in the art. For example, a dehydrating apparatus having an inlet inputting the algae biomass, which is larger than an outlet, is effective for removing water from the algae biomass and to further facilitate the cutting operation.

In one example, a washing operation may be further included to remove impurities from the algae biomass prior to the dehydration operation. The algae biomass may be washed with seawater or freshwater or a combination of freshwater and seawater.

Here, the washing and dehydration operations may be continuously performed in one apparatus. For example, the algae biomass may be input to a dehydrating apparatus, and seawater and freshwater may be sequentially input to the dehydrating apparatus to wash the algae biomass, followed by removing the water contained in the algae biomass and water input to wash the algae biomass. To this end, the dehydrating apparatus may include at least one inlet through which seawater or freshwater is input to wash the algae biomass, and at least one outlet through which water in the algae biomass is output.

The dehydrating apparatus may be rotated to uniformly wash the algae biomass.

After the dehydration operation, a cutting operation is performed for effective saccharification. In the cutting operation the dehydrated algae biomass is cut to a predetermined size to increase the specific surface area of the algae biomass. A cutting apparatus for the cutting operation may have an inlet inputting the algae biomass, a cutter cutting the algae biomass, and an outlet outputting the algae biomass. The cutter may include at least one knife. A plurality of cutters may be disposed a predetermined distance apart from each other vertically or horizontally. For example, a plurality of cutters which each move vertically may be disposed in a horizontal manner. In addition, the cutting apparatus may be directly or indirectly connected with the dehydrating apparatus via a conveying apparatus, such as a conveyer belt, which continuously provides and outputs the The size of the cut algae biomass is not particularly limited, but may be in the range from about $1 \times 1 \times 1$ cm$^3$ to about $10 \times 10 \times 10$ cm$^3$.

The algae biomass cut by the cutting operation is subjected to a saccharification operation and converted into monosaccharide. The saccharification operation includes direct saccharification to directly extract monosaccharide from the algae biomass, and indirect saccharification to extract polysaccharide from the algae biomass. Monosaccharide is then extracted from the polysaccharide. The saccharification operation may be performed in one or multiple stages.

The monosaccharide or polysaccharide may vary according to the kind and elements of the algae biomass. For example, the polysaccharide may be at least one selected from the group consisting of agar, cellulose, starch, carrageenan, alginic acid and fibrine, but the disclosed concept is not limited thereto. The monosaccharide may be at least one selected from the group consisting of glucose, galactose, galactose derivatives, 3,6-anhydrogalactose, fucose, rhamnose, xylose, arabinose and mannose, but the disclosed concept is not limited thereto.

The saccharification operation is performed through hydrolysis using a hydrolysis catalyst and/or a hydrolase. For example, only monosaccharide may be yielded, or both monosaccharide and polysaccharide may be yielded by inputting a hydrolysis catalyst and a hydrolase to the cut algae biomass. Here, the polysaccharide may be further converted into monosaccharides by hydrolysis using a hydrolysis catalyst or a hydrolase.

Examples of the hydrolase may include, but are not limited to, α-amylase, glucoamylase, endoglucanase, cellulase, xylanase, β-glucosidase, α-agarase, β-agaraase I, β-agarase II, β-galactosidase, neoagarobiose, neoagarotetraose, neoagarohexaose, and α-neoagarobiose hydrolase.

The saccharification operation may be performed by acid hydrolysis using a hydrolysis catalyst containing, for example, an undiluted acid or a solid acid.

Conventionally, a diluted liquid acid is used to saccharify dried and pulverized algae biomass. However, when using the diluted liquid acid, a large quantity of solvent is utilized, so that the sugar concentration is low. In order to increase the sugar concentration, a concentration operation for removing the solvent is further required.

On the other hand, according to the exemplary embodiment, algae biomass having a water content of about 10% to about 70% by weight is utilized, so that a solvent is not necessary and an undiluted acid or a solid acid can be used.

The solid or undiluted acid may react with water contained in the algae biomass to produce liquid acid through a hydration reaction. For example, as shown in the following reaction, the undiluted sulfur trioxide is changed into sulfuric acid by a hydration reaction:

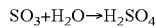

That is, when using the undiluted acid or solid acid, no solvent is used to control the acid concentration and solvent removal is not necessary after saccharification, and thus a decrease in sugar concentration is prevented.

For example, when the algae biomass having a water content of nearly 0% by weight through dehydration is treated with about 1 to 5% weak acid for saccharification, a large quantity of solvent equaling 30 to 70 times the algae biomass is used. This results in a sugar concentration of only about 0.5 to 0.6%.

On the other hand, according to an exemplary embodiment, when the algae biomass having a water content of about 40% to about 50% by weight is utilized, the quantity of solvent used is just 5 to 7 times larger than the quantity of the algae biomass, and the resulting sugar concentration is about 4% to about 6%, which is about 9 to 10 times higher than in the above example. Accordingly, the cost of distilling solvent can be considerably reduced.

The type of acid is not particularly limited and may be at least one selected from the group consisting of sulfur trioxide (SO$_3$), sulfamic acid, citric acid, succinic acid, maleic acid and phthalic acid. The amount of the acid input may depend on the water content and elements of the algae biomass and the acid concentration may be controlled to be about 0.5% to about 10% by weight or about 1% to about 5% by weight.

The saccharification may be performed at about 80 to 200° C. and at about 1 to 10 bar for about 0.5 to 24 hours or about 1 to 5 hours. The saccharification may be optionally performed in vapor at about 100 to 250° C.

Through such saccharification, monosaccharides may be directly retrieved, or through multiple-stage saccharification, monosaccharides may be obtained from polysaccharides. In one example, liquid monosaccharide such as galactose and solid polysaccharide such as cellulose may be obtained. The polysaccharide, cellulose, may be converted into the monosaccharide, glucose, by hydrolysis using a hydrolase such as cellulase.

2. Method of Producing Biofuel

In another exemplary embodiment, a method of producing biofuel using the monosaccharide or polysaccharide obtained by the above-described method is provided.

In one example, biofuel such as ethanol may be produced from monosaccharides such as glucose and galactose through fermentation using microorganisms.

As described above, the monosaccharide may be at least one selected from the group consisting of glucose, galactose, galactose derivatives, 3,6-anhydrogalactose, fucose, rhamnose, xylose, glucuronic acid, arabinose and mannose.

The fermentation is an operation of fermenting monosaccharide such as glucose produced by saccharification using a microorganism such as yeast to be converted into alcohol, as follows:

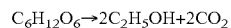

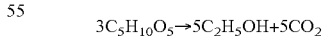

Biofuel is fuel prepared using biomass as a raw material, which may include C1-C4 alcohols, C2-C4 ketones, olefins and esters. To be specific, examples of biofuels may include, but are not limited to, ethanol, propanol, isopropanol, butanol, acetone, ethylene, propylene, and fatty acid methyl ester.

Microorganisms used for fermentation of the monosaccharide may depend on the type of the monosaccharide, and thus various microorganisms well known in the art may be used.

Examples of the microorganism may include, but are not limited to, *Saccharomyces cerevisiae*, *Klebsiella oxytoca* P2,

*Brettanomyces curstersii, Saccharomyces uvzrun, Candida brassicae, Sarcina ventriculi, Zymomonas mobilis, Kluyveromyces marxianus* IMB3, *Clostridium acetobutylicum, Clostridium beijerinckii, Kluyveromyces fragilis, Brettanomyces custersii, Clostriduim aurantibutylicum* and *Clostridium tetanomorphum.*

In addition, the saccharification and fermentation may be performed in separate reaction vessels through separate hydrolysis and fermentation (SHF) processes, or in one reaction vessel through a simultaneous saccharification and fermentation (SSF) process.

In the SHF process, saccharification and fermentation may be performed under optimized conditions, and however end-product inhibition of the enzymes in the enzymatic hydrolysis may occur. Thus, more enzymes are needed to overcome this inhibition, which is uneconomical. For example, due to end-product inhibition from the intermediate product, cellobiose, and the final product, glucose, the enzymatic hydrolysis reaction may be terminated according to the increase of the glucose concentration.

On the other hand, in the SSF process, as soon as glucose is produced in saccharification, yeast consumes the glucose in fermentation and thus sugar accumulation in a reaction vessel can be minimized. As a result, end-product inhibition in the SHF process can be avoided, and hydrolysis mediated by a hydrolase (enzyme) can be enhanced. Further, the SSF process can reduce production costs due to low equipment costs and low input of enzyme, and can also reduce the risk of contamination due to ethanol in the reaction vessel.

Optionally, purification may be further performed to purify a fermentation broth yielded from the fermentation, according to a method known in the art.

3. Apparatus for Pre-Treating and Saccharifying Algae Biomass

Figure 2:
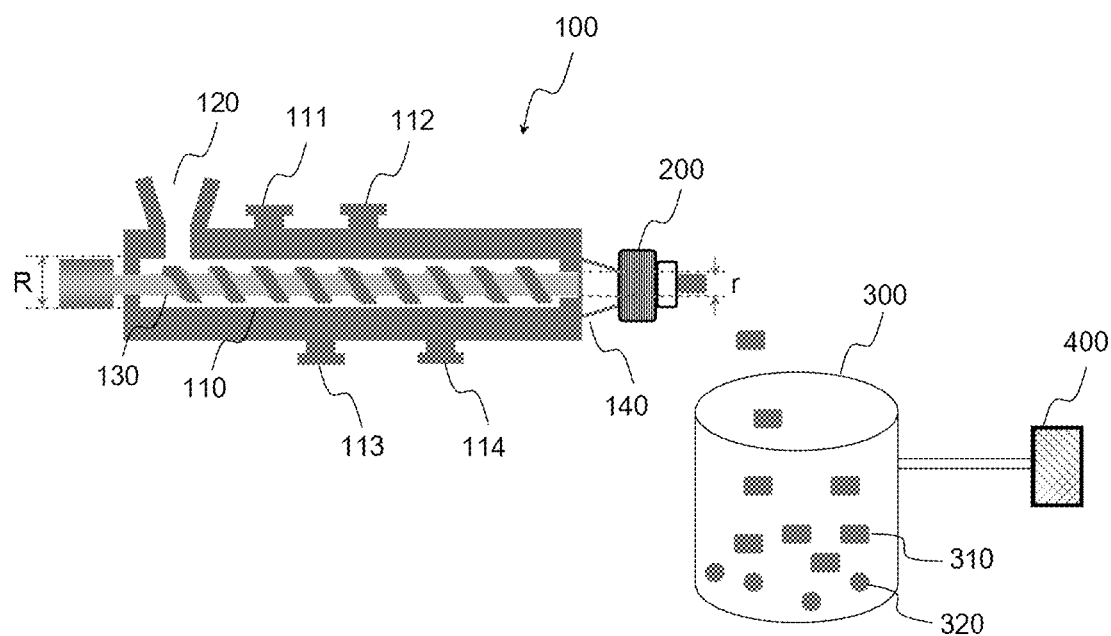
FIG. 2 is a schematic view of an exemplary embodiment of an apparatus for pre-treating and saccharifying algae biomass according to the disclosure.

In another exemplary embodiment, an apparatus for pre-treating and saccharifying algae biomass is provided. FIG. 2 is a schematic view of a pre-treatment and saccharifying apparatus according to an exemplary embodiment, which will be described in detail below.

The apparatus for pre-treating and saccharifying algae biomass according to the exemplary embodiment includes: a dehydrating apparatus 100 including a hollow conduit 110 through which algae biomass flows, an inlet 120 disposed at one side of the conduit 110 to input the biomass therethrough, a screw 130 disposed in the hollow center of the conduit 110 to provide a biomass conveying force by axial rotation, and an outlet 140 disposed at the other side of the conduit 110 and outputting the biomass; a cutting apparatus 200 connected to an end of the outlet 140 of the dehydrating apparatus 100 to cut the biomass; a saccharifying apparatus 300 including a reaction vessel containing the biomass cut by the cutting apparatus to saccharify the cut biomass; and a vapor generating apparatus 400 connected to the saccharifying apparatus 300 to provide vapor thereto.

When the algae biomass is input to the dehydrating apparatus 100 through the inlet 120, it is conveyed to the outlet 140 by rotation of the screw 130. Here, water may be removed by centrifugal force during the rotation of the screw 130. Due to a difference between an amount of algae biomass conveyed and an amount output, pressure may be applied to the outlet, and thus water may be removed from the algae biomass.

In one example, the conduit 110 of the dehydrating apparatus 100 may include at least one inlets 111 and 112 and at least one outlets 113 and 114. Seawater and freshwater may be sequentially input to the conduit 110 of the dehydrating apparatus 100 through the inlets 111 and 112 to wash the algae biomass. That is, washing may be performed in the dehydrating apparatus 100. Thus, seawater may be input to a first inlet 111 formed in the conduit 110, and freshwater may be input to a second inlet 112 for washing. After washing the algae biomass, seawater, freshwater and water contained in the algae biomass are removed through the outlets 113 and 114.

The inlet 120 and the outlet 140 of the dehydrating apparatus 100 may be formed in various shapes including circular, triangular and rectangular shapes, and thus the shape of the outlet 140 may be designed to correspond to a desired cut shape of the biomass.

Figure 3:
FIG. 3 is a schematic view of an exemplary embodiment of a dehydrating apparatus according to the disclosure.

In one example, the conduit 110 may be wider at an inlet 120 side than at an outlet 140 side. For example, when the conduit 110 is formed in a cylinder shape, an inner diameter R of the inlet side may be larger than an inner diameter r of the outlet side. In another example, the inner diameter of the conduit 110 may be gradually decreased from the inlet side toward the outlet side as shown in FIG. 3.

Here, since an area of the outlet side of the dehydrating apparatus 100 is decreased, the output of the algae biomass is reduced and pressure is applied to the algae biomass, thereby effectively removing water. Further, when the inner diameter r of the outlet side closely corresponds to a cut size, the cut size may be easily adjusted in a subsequent cutting operation. For example, a ratio of the inner diameter R of the inlet side to an inner diameter r of the outlet side maybe about 1.5:1 to about 20:1, or about 2:1 to about 10:1.

The cutting apparatus 200 is not particularly limited and may include a cutter known in the art. For example, the cutting apparatus 200 may include an inlet inputting the algae biomass, a cutter cutting the algae biomass, and an outlet outputting the algae biomass. The cutter may be at least one knife. A plurality of cutters may be disposed at regular intervals vertically or horizontally. For example, a plurality of cutters, each of which moves vertically, may be disposed horizontally Meanwhile, the cutting apparatus 200 in FIG. 2 may be directly connected to an end of the outlet 140 side of the dehydrating apparatus 100; however, the inventive concept is not limited to such a configuration. Alternatively, the cutting apparatus 200 may be indirectly connected via a conveyer apparatus, such as a conveyer belt (not shown), continuously providing and outputting the algae biomass. The cut size of the algae biomass maybe about $1 \times 1 \times 1$ cm$^3$ to about $10 \times 10 \times 10$ cm$^3$.

The saccharifying apparatus 300 includes a reaction vessel in which the algae biomass 310 cut to a predetermined size by the cutting apparatus 200 is saccharified by reaction with a hydrolysis catalyst and/or a hydrolase 320.

A reaction vessel of the saccharifying apparatus 300 may be connected with the vapor generating apparatus 400 to maintain a reaction temperature and provide moisture to the reaction vessel. The vapor generating apparatus 400 may use steam, which is known in the art, but the inventive concept is not limited thereto.

The inventive concept will be described in detail below with reference to examples.

COMPARATIVE EXAMPLE 1

A *Gelidium amansii* sample was completely dried for 24 hours using a 40° C. hot air dryer and pulverized using a pulverizer, thereby obtaining *Gelidium amansii* powder. For saccharification, 5 g of the *Gelidium amansii* powder and 200 ml of 1% sulfuric acid solution were put into a reaction vessel in a ratio of 1:40 to react at about 121° C. for 30 minutes, and then cooled to room temperature.

INVENTIVE EXAMPLE 1

A *Gelidium amansii* sample was dehydrated to have a water content of about 50% and then cut into a size of 1×1×1 cm³. For saccharification, 5 g of the cut *Gelidium amansii* sample and 0.1 g of undiluted acid, SO₃, were put into a reaction vessel to react in vapor at about 120° C. for 30 minutes and then cooled to room temperature.

EXPERIMENTAL EXAMPLE 1

Reaction mixtures were prepared using the saccharified solutions yielded from Inventive Example 1 and Comparative Example 1, followed by dinitrosalicylic acid (DNS) colorimetric analysis for measuring reducing sugar concentration. The colorimetric analysis utilizes a color change when 3,5-dinitrosalicylic acid (DNS) is reduced to 3-amino, 5-nitro-salicylic acid under alkali conditions. A quantitative analysis of sugar in the reaction mixture is then performed by a spectrophotometric (colorimetric) method. After that, sugar concentrations in the reaction mixtures are calculated on the basis of the following Formula 1, and the results are summarized in Table 1.

$$\text{Sugar concentration (g/L)} = \frac{\text{Produced reducing sugar (g)}}{\text{Saccharification reaction mixture (L)}} \quad \text{Formula 1}$$

TABLE 1

| Biomass | Ratio of biomass to solvent for pre-treatment with 1% (wt) weak acid | Sugar concentration (g/L) |
|---|---|---|
| Comparative Example 1 (Dry *Gelidium amansii*) | 1:40 | 5 |
| Inventive Example 1 (Wet *Gelidium amansii*) | 1:5 | 45 |

As seen from Table 1, Comparative Example 1 shows that, for pre-treatment with 1% by weight weak acid, 40 times more solvent than biomass was required, and the sugar concentration was calculated to be only 0.5% by weight.

On the other hand, since *Gelidium amansii* having a water content of about 50% by weight was used, Inventive Example 1 did not need solvent for pre-treatment with 1% weak acid. Thus, as shown in Table 1, only about 5 times more solvent than biomass was used, and sugar concentration increased 9 times as compared to Comparative Example 1.

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims. Moreover, all combinations of the above-described elements and all possible variations thereof are encompassed by the inventive concept unless otherwise indicated herein or by context.

What is claimed is:

1. A method of pre-treating and saccharifying an algae biomass, comprising:
    dehydrating the algae biomass to have a water content of about 10% to about 70% by weight;
    cutting the algae biomass having a water content of about 10% to about 70% by weight to a predetermined size; and
    saccharifying the cut algae biomass using a solid acid to yield a monosaccharide, wherein the solid acid is added to the dehydrated algae biomass having a water content of about 10% to about 70% by weight.

2. The method of claim 1, wherein the algae biomass is dehydrated to have a water content of about 20% to about 60% by weight.

3. The method of claim 1, wherein dehydrating the algae biomass is performed in a dehydrating apparatus having a screw providing a conveying force by axial rotation at a temperature of about 15 to 35° C. for about 0.5 to about 100 minutes.

4. The method of claim 1, further comprising washing the algae biomass by sequentially treating the algae biomass with seawater and freshwater before dehydrating.

5. The method of claim 4, wherein washing and dehydrating the algae biomass is sequentially performed in a dehydrating apparatus.

6. The method of claim 1, wherein the algae biomass is cut into a size of about 1×1×1 cm³ to about 10×10×10 cm³.

7. The method of claim 1, wherein the monosaccharide is at least one selected from the group consisting of glucose, galactose, galactose derivatives, 3, 6-anhydrogalactose, fucose, rhamnose, xylose, glucuronic acid, arabinose, mannose and any combinations thereof.

8. The method of claim 1, wherein the solid acid is at least one selected from the group consisting of sulfuric anhydride (SO₃), sulfamic acid, citric acid, succinic acid, maleic acid, phthalic acid and any combinations thereof.

9. The method of claim 1, wherein the solid acid is added to the algae biomass in an amount of about 0.5% to about 10% by weight.

10. The method of claim 1, wherein saccharifying the algae biomass is performed at a temperature of about 80 to 200° C. and a pressure of about 1 to 10 bar for about 0.5 to 5 hours.

11. The method of claim 1, wherein saccharifying the algae biomass is performed under vapor, and the temperature of the vapor is about 100 to about 250° C.

12. The method of claim 1, further comprising fermenting the monosaccharide with a microorganism to form a biofuel.

13. The method of claim 12, wherein the biofuel is selected from the group consisting of ethanol, propanol, isopropanol, butanol, acetone, ethylene, propylene and fatty acid methyl ester.

14. The method of claim 12, wherein the microorganism is at least one selected from the group consisting of *Saccharomyces cerevisiae*, *Klebsiella oxvtoca*P2, *Brettanomyces curstersii*, *Saccharomyces uvzrun*, *Candida brassicae*, *Sarcina ventriculi*, *Zvmomonas mobilis*, *Kluyveromvces marxianus* IMB3, *Clostridium acetobutvlicum*, *Clostridium beijerinckii*, *Kluyveromvces fragilis*, *Brettanomyces custersii*, *Clostriduim aurantibutylicum*, *Clostridium tetanomorphum* and any combinations thereof.

* * * * *